(12) United States Patent
Gutterer

(10) Patent No.: US 6,191,138 B1
(45) Date of Patent: Feb. 20, 2001

(54) PHENANTHRIDINES

(75) Inventor: Beate Gutterer, Allensbach (DE)

(73) Assignee: Byk Gulden Lomberg Chemische Fabrik GmbH, Constance (DE)

(*) Notice: Under 35 U.S.C. 154(b), the term of this patent shall be extended for 0 days.

(21) Appl. No.: 09/117,507

(22) PCT Filed: Jan. 30, 1997

(86) PCT No.: PCT/EP97/00402
§ 371 Date: Jul. 31, 1998
§ 102(e) Date: Jul. 31, 1998

(87) PCT Pub. No.: WO97/28131
PCT Pub. Date: Aug. 7, 1997

(30) Foreign Application Priority Data

Jan. 31, 1996 (DE) ............................................. 196 03 321
Feb. 8, 1996 (EP) ................................................ 96101791

(51) Int. Cl.[7] ...................... C07D 221/12; C07D 474/04; A61K 31/47
(52) U.S. Cl. ........................... 514/287; 514/291; 546/65; 546/109
(58) Field of Search ..................... 546/65, 109; 514/287, 514/291

(56) References Cited

FOREIGN PATENT DOCUMENTS

| 0045171 | * | 2/1982 | (EP) | ..................................... 546/109 |
| WO 97/28131 | * | 2/1982 | (WO) | ..................................... 546/109 |

* cited by examiner

Primary Examiner—Alan L. Rotman
(74) Attorney, Agent, or Firm—Jacobson, Price, Holman & Stern, PLLC

(57) ABSTRACT

Compounds of formula (I), where R1, R2, R3, R31, R4, R5, R51 and R6 have the meanings given in the description, are new active bronchial therapeutic agents.

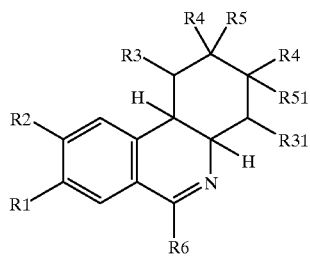

(I)

12 Claims, 1 Drawing Sheet

(I)

(II)

(III)

(IV)

(IVa)

(V)

R3-CH=C(R4)-C(R4)=CH-R31 (VI)

(VII)

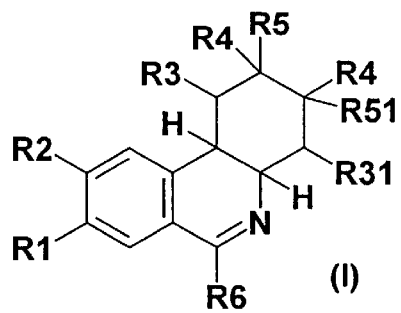
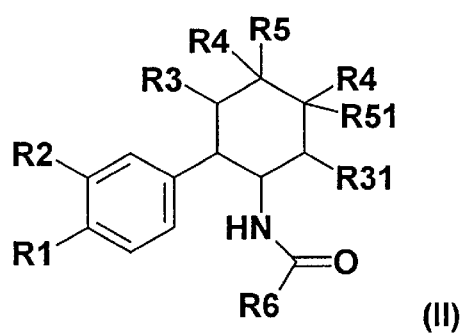
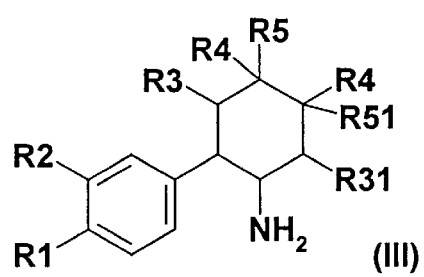
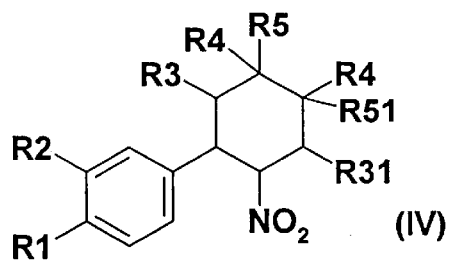
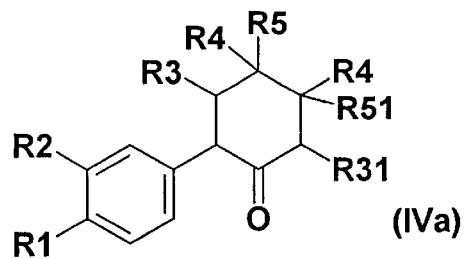
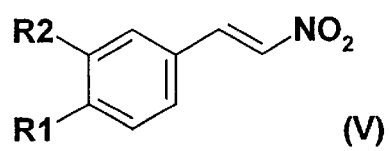
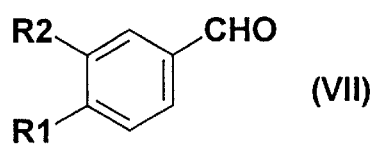

PHENANTHRIDINES

RELATED APPLICATION

This application has subject matter related to that disclosed and claimed in co-pending application Ser. No. 08/142,206, filed Sep. 3, 1998.

FIELD OF APPLICATION OF THE INVENTION

The invention relates to novel 6-phenylphenanthridines which are used in the pharmaceutical industry for the production of medicaments.

KNOWN TECHNICAL BACKGROUND

The synthesis of 6-phenylphenanthridines is described in Chem. Ber. 1939, 72, 675–677, J. Chem. Soc., 1956, 4280–4283 and J. Chem. Soc. (C), 1971, 1805–1808.

DESCRIPTION OF THE INVENTION

It has now been found that the novel phenanthridines described in greater detail below have surprising and particularly advantageous properties.

The invention thus relates to compounds of the formula I (see attached formula sheet), in which
R1 is hydroxy, 1–4C-alkoxy, 3–7C-cycloalkoxy or 3–7C-cycloalkylmethoxy or 1–4C-alkoxy which is completely or partially substituted by fluorine,
R2 is hydroxy, 1–4C-alkoxy, 3–7C-cycloalkoxy or 3–7C-cycloalkylmethoxy or 1–4C-alkoxy which is completely or partially substituted by fluorine,
or in which
R1 and R2 together are a 1–2C-alkylenedioxy group,
R3 is hydrogen or 1–4C-alkyl,
R31 is hydrogen or 1–4C-alkyl,
or in which
R3 and R31 together are a 1–4C-alkylene group,
R4 is hydrogen or 1–4C-alkyl,
R5 is hydrogen
R51 is hydrogen,
or in which
R5 and R51 together are an additional bond,
R6 is a phenyl radical which is substituted by R7, where
R7 is COOR71 or CON(R72)R73 and R71 is hydrogen, 1–7C-alkyl, 3–7C-cycloalkyl or 3–7C-cycloalkylmethyl and R72 and R73 independently of one another are each hydrogen, 1–7C-alkyl, 3–7C-cycloalkyl or 3–7C-cycloalkylmethyl,
and the salts of these compounds.

1–4C-alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and preferably the ethoxy and methoxy radical.

3–7C-cycloalkoxy represents, for example, cyclopropyloxy, cyclobutyloxy, cyclopentyloxy, cyclohexyloxy and cycloheptyloxy, and preferably cyclopropyloxy, cyclobutyloxy and cyclopentyloxy.

3–7C-cycloalkylmethoxy respresents, for example, cyclopropylmethoxy, cyclobutylmethoxy, cyclopentylmethoxy, cyclohexylmethoxy and cycloheptylmethoxy, and preferably cyclopropylmethoxy, cyclobutylmethoxy and cyclopentylmethoxy.

1–4C-alkoxy which is completely or partially substituted by fluorine is, for example, the 1,2,2-trifluoroethoxy, the 2,2,3,3,3-pentafluoropropoxy, the perfluoroethoxy, the 1,1, 2,2-tetrafluoroethoxy, the trifluoromethoxy and in particular the 2,2,2-trifluoroethoxy and preferably the difluoromethoxy radical.

1–4C-alkyl represents a straight-chain or branched alkyl radical having 1 to 4 carbon atoms. Examples which may be mentioned are the butyl, isobutyl, sec-butyl, tert-butyl, propyl, isopropyl and preferably the ethyl and methyl radical.

1–2C-alkylenedioxy represents, for example, the methylenedioxy (—O—$CH_2$—O—) and the ethylenedioxy radical (—O—$CH_2$—$CH_2$—O—).

If R3 and R31 together have the meaning 1–4C-alkylene, positions 1 and 4 in compounds of the formula I are linked with each other by a 1–4C-alkylene bridge, and 1–4C-alkylene represents straight-chain or branched alkylene radicals having 1 to 4 carbon atoms. Examples which may be mentioned are the radicals methylene (—$CH_2$—), ethylene (—$CH_2$—$CH_2$—), trimethylene (—$CH_2$—$CH_2$—$CH_2$—), 1,2-dimethylethylene [—$CH(CH_3)$—$CH(CH_3)$—] and isopropylidene [—$C(CH_3)_2$—].

If R5 and R51 together denote an additional bond, the carbon atoms in positions 2 and 3 of the compounds of the formula I are linked with one another via a double bond.

1–7C-alkyl represents straight-chain or branched alkyl radicals having 1 to 7 carbon atoms. Examples which may be mentioned are the heptyl, isoheptyl (2-methylhexyl), hexyl, isohexyl (2-methylpentyl), neohexyl (2,2-dimethylbutyl), pentyl, isopentyl (3-methylbutyl), neopentyl (2,2-dimethylpropyl), butyl, isobutyl, sec-butyl, tert-butyl, propyl, isopropyl, ethyl and the methyl radical.

3–7C-cycloalkyl represents the cyclopropyl, cyclobutyl, cyclopentyl, cyclohexyl and cycloheptyl radical. Preference is given to the 3–5C-cycloalkyl radicals, cyclopropyl, cyclobutyl and cyclopentyl.

3–7C-cycloalkylmethyl represents a methyl radical which is substituted by one of the abovementioned 3–7C-cycloalkyl radicals. Preference is given to the 3–5C-cycloalkylmethyl radicals, cyclopropylmethyl, cyclobutylmethyl and cyclopentylmethyl.

The substituent R7 may be attached to any suitable position on the phenyl ring. Particular preference is given to the substituent R7 attached in position 4 of the phenyl ring.

Examples of R7-substituted phenyl radicals which may be mentioned are 4-carboxyphenyl, 3-carboxyphenyl, 4-methoxycarbonylphenyl, 3-methoxycarbonylphenyl, 2-methoxycarbonylphenyl, 4-ethoxycarbonylphenyl, 3-ethoxycarbonylphenyl, 2-ethoxycarbonylphenyl, 4-(N-methylaminocarbonyl)phenyl, 3-(N-methylaminocarbonyl)phenyl, 4-(N,N-dimethylaminocarbonyl)phenyl, 4-carbamoylphenyl and 3-carbamoylphenyl.

Compounds of the formula I to be emphasized are those in which
R1 is 1–4C-alkoxy, 3–7C-cycloalkoxy or 3–7C-cycloalkylmethoxy or 1–2C-alkoxy which is completely or partially substituted by fluorine,
R2 is 1–4C-alkoxy, 3–7C-cycloalkoxy or 3–7C-cycloalkylmethoxy or 1–2C-alkoxy which is completely or partially substituted by fluorine,
R3 is hydrogen,
R31 is hydrogen,
or in which
R3 and R31 together are a 1–2C-alkylene group,
R4 is hydrogen or 1–4C-alkyl,
R5 is hydrogen,
R51 is hydrogen,
or in which
R5 and R51 together are an additional bond, R6 is a phenyl radical which is substituted by R7, where
R7 is COOR71 or CON(R72)R73 and R71 is hydrogen, 1–7C-alkyl or 3–7C-cycloalkylmethyl and R72 and R73 independently of one another are each hydrogen or 1–7C-alkyl,
and the salts of these compounds.

Compounds of the formula I which are particularly to be emphasized are those in which
R1 is 1–4C-alkoxy, 3–7C-cycloalkoxy or 1–2C-alkoxy which is completely or partially substituted by fluorine,
R2 is 1–4C-alkoxy, 3–7C-cycloalkoxy or 1–2C-alkoxy which is completely or partially substituted by fluorine,
R3 is hydrogen,
R31 is hydrogen,
or in which
R3 and R31 together are a 1–2C-alkylene group,
R4 is hydrogen or 1–4C-alkyl,
R5 is hydrogen,
R51 is hydrogen,
or in which
R5 and R51 together are an additional bond,
R6 is a phenyl radical which is substituted by R7, where
R7 is COOR71 or CON(R72)R73 and R71 is hydrogen, 1–7C-alkyl or 3–7C-cycloalkylmethyl and R72 and R73 independently of one another are each hydrogen or 1–4C-alkyl,
and the salts of these compounds.

Preferred compounds of the formula I are those in which
R1 is methoxy, ethoxy or difluoromethoxy,
R2 is methoxy, ethoxy or difluoromethoxy,
R3 and R31 are each hydrogen,
R4 is hydrogen,
R5 and R51 are each hydrogen,
R6 is a phenyl radical which is substituted by R7, where
R7 is COOR71 or CON(R72)R73 and R71 is hydrogen or 1–4C-alkyl, R72 is hydrogen and R73 is 1–4C-alkyl,
and the salts of these compounds.

An embodiment of the preferred compounds of the formula I are those in which
R1 is methoxy or ethoxy,
R2 is methoxy, ethoxy or difluoromethoxy,
R3 and R31 are each hydrogen,
R4 is hydrogen,
R5 and R51 are each hydrogen,
R6 is a phenyl radical which is substituted by R7, where
R7 is COOR71 and R71 is hydrogen or 1–4C-alkyl,
and the salts of these compounds.

Suitable salts of compounds of the formula I—depending on substitution—are all acid addition salts or all salts with bases. The pharmacologically tolerable salts of the inorganic and organic acids and bases customarily used in pharmacy may be mentioned particularly. Those suitable are on the one hand water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, the acids being employed in the salt preparation—depending on whether it is a mono- or polybasic acid and depending on which salt is desired—in an equimolar quantitative ratio or one differing therefrom.

On the other hand, salts with bases are also suitable. Examples of salts with bases which may be mentioned are alkali metal (lithium, sodium, potassium) or calcium, aluminum, magnesium, titanium, ammonium, meglumine or guanidinium salts, here also in the salt preparation the bases being employed in an equimolar quantitative ratio or one differing therefrom.

Pharmacologically intolerable salts which can be initially obtained, for example, as process products in the preparation of the compounds according to the invention on an industrial scale, are converted into pharmacologically tolerable salts by processes known to the person skilled in the art.

The compounds of the formula I are chiral compounds having chiral centers in positions 4a and 10b and, depending on the meaning of the substituents R3, R31, R4, R5 and R51, further chiral centers in positions 1, 2, 3 and 4. The invention therefore embraces all feasible pure diastereomers and pure enantiomers and also mixtures thereof in any mixing ratio, including the racemates. Preference is given to the compounds of the formula I in which the hydrogen atoms in positions 4a and 10b are cis to each other. Particular preference is given here to the pure cis diastereomers and the pure cis enantiomers and also mixtures thereof in any mixing ratio, including the racemates. Preference is given here to the (−)-cis enantiomers.

The enantiomers can be separated in a known manner (for example by preparation and separation of appropriate diastereoisomeric compounds). A separation of enantiomers is preferably carried out at the stage of the starting materials of the formula III (see attached formula sheet). Alternatively, enantiomerically pure starting materials of the formula III can also be prepared by asymmetric syntheses.

The invention furthermore provides a process for preparing the compounds of the formula I in which R1, R2, R3, R31, R4, R5, R51 and R6 are each as defined above, and the salts thereof. The process comprises cyclocondensing compounds of the formula II (see attached formula sheet) in which R1, R2, R3, R31, R4, R5, R51 and R6 are each as defined above and, if desired, then converting compounds of the formula I obtained into their salts or, if desired, then converting salts of the compounds of the formula I obtained into the free compounds.

If desired, compounds of the formula I obtained can be converted into further compounds of the formula I by derivatization. For example, the corresponding acids can be obtained from compounds of the formula I in which R7 is an ester group by acidic or alkaline hydrolysis, or the corresponding amides can be prepared by reaction with amines of the formula HN(R72)R73, or else corresponding esters can be prepared by transesterification of esters of the formula I or by esterification of acids of the formula I. The reactions are advantageously carried out analogously to methods known to the person skilled in the art, for example as described in the examples below.

The cyclocondensation is carried out in a manner known per se to the person skilled in the art according to Bischler-Napieralski (e.g. as described in J. Chem. Soc., 1956, 4280–4282) in the presence of a suitable condensing agent, such as, for example, polyphosphoric acid, phosphorus pentachloride, phosphorus pentoxide or preferably phosphorus oxytrichloride, in a suitable inert solvent, for example in a chlorinated hydrocarbon such as chloroform, or in a cyclic hydrocarbon such as toluene or xylene, or another inert solvent such as acetonitrile, or without a further solvent using an excess of condensing agent, preferably at elevated temperature, in particular at the boiling point of the solvent or condensing agent used.

The substances according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

Salts are obtained by dissolving the free compound in a suitable solvent, for example in a chlorinated hydrocarbon, such as methylene chloride or chloroform, or a low molecular weight aliphatic alcohol (methanol, ethanol, isopropanol) which contains the desired acid or base, or to which the desired acid or base is subsequently added. The salts are obtained by filtering, reprecipitating, precipitating with a nonsolvent for the addition salt or by evaporating the solvent. Salts obtained can be converted into the free compounds, which in turn can be converted into salts, by alkalization or by acidification. In this manner, pharmacologically intolerable salts can be converted into pharmacologically tolerable salts.

Compounds of the formula II (see attached formula sheet) in which R1, R2, R3, R31, R4, R5, R51 and R6 are each as defined above can be obtained from the corresponding compounds of the formula III (see attached formula sheet) in which R1, R2, R3, R31, R4, R5 and R51 are each as defined above by reaction with compounds of the formula R6—CO—X in which R6 is as defined above and X is a suitable leaving group, preferably a chlorine atom. The benzoylation, for example, is carried out as described in the examples below or in J. Chem. Soc. (C), 1971, 1805–1808.

Compounds of the formula R6—CO—X and compounds of the formula III are either known or can be prepared in a manner known per se.

The compounds of the formula III can be prepared, for example, from compounds of the formula IV (see attached formula sheet) in which R1, R2, R3, R31, R4, R5 and R51 are each as defined above by reduction of the nitro group.

The reduction is carried out in a manner known to the person skilled in the art, for example as described in J. Org. Chem. 1962, 27, 4426 or in the examples below. The reduction is preferably carried out by catalytic hydrogenation, for example in the presence of Raney nickel, in a lower alcohol such as methanol or ethanol at room temperature and under atmospheric or elevated pressure. If desired, a catalytic amount of an acid, such as, for example, hydrochloric acid, can be added to the solvent.

Enantiomerically pure compounds of the formula III are obtained in a manner known to the person skilled in the art, for example via salt formation of the racemic compounds of the formula III with optically active carboxylic acids.

Alternatively, enantiomerically pure compounds of the formula III can also be obtained by asymmetric synthesis starting from compounds of the formula IVa (see attached formula sheet) by imine formation with optically active amines (for example R-(+)-1-phenethylamine and S-(-)-1-phenethylamine, followed by hydrogenation and subsequent reductive cleavage of the secondary amine obtained (as described, for example, in Arch. Pharm. 1989, 322, 187 or in the examples below).

Compounds of the formula IVa can be obtained, for example, starting from compounds of the formula IV in a manner known to the person skilled in the art (for example as described in Tetrahedron 1968, 24, 6583 or in the examples).

The compounds of the formula IV (see attached formula sheet) in which R1, R2, R3, R31 and R4 are each as defined above and R5 and R51 are hydrogen are either known, or they can be prepared from corresponding compounds of the formula IV in which R5 and R51 together denote a further bond. The reaction can be carried out in a manner known to the person skilled in the art, preferably by hydrogenation in the presence of a catalyst, such as, for example, palladium on activated carbon, as described, for example, in J. Chem. Soc.(C), 1971, 1805–1808 or in the examples below.

The compounds of the formula IV in which R5 and R51 together denote a further bond are either known or they can be obtained by reaction of compounds of the formula V (see attached formula sheet) in which R1 and R2 are as defined above with compounds of the formula VI (see attached formula sheet) in which R3, R31 and R4 are each as defined above.

The cycloaddition is carried out in a manner known to the person skilled in the art in accordance with Diels-Alder, as described, for example, in J. Amer. Chem. Soc. 1957, 79, 6559 or in J. Org. Chem. 1952, 17, 581, or in the examples below.

Compounds of the formula IV obtained in the cycloaddition having the phenyl ring and the nitro group trans to one another can be converted into the corresponding cis compounds in a manner known to the person skilled in the art, as described, for example, in J. Amer. Chem. Soc. 1957, 79, 6559 or in the examples below.

The compounds of the formulae VI and V are either known or can be prepared in a known manner. The compounds of the formula V, for example, can be prepared from corresponding compounds of the formula VII in a manner known to the person skilled in the art, as described, for example, in J. Chem. Soc. 1951, 2524 or in J. Org. Chem. 1944, 9, 170, or in the examples below.

The compounds of the formula VII (see attached formula sheet) in which R1 and R2 are each as defined above are either known, or they can be prepared in a manner known to the person skilled in the art, as described, for example, in Ber. Dtsch. Chem. Ges. 1925, 58, 203 or in the examples below.

The following examples serve to illustrate the invention in greater detail without restricting it. Further compounds of the formula I, whose preparation is not explicitly described, can also be prepared in a similar manner or in a manner familiar per se to the person skilled in the art using customary process techniques.

In the examples, m.p. stands for melting point, of Th. for of theory, b.p. for boiling point, h for hour(s), RT for room temperature, EF for empirical formula, MW for molecular weight, calc. for calculated. The compounds mentioned in the examples and their salts are the preferred subject of the invention.

EXAMPLES

Final products 1. (+/-)-cis-8,9-dimethoxy-6-[4-(methoxycarbonyl) phenyl]-1,2,3,4,4a,10b-hexahydrophenanthridine 1.8 g of (+/-)-cis-N-[2-(3,4-dimethoxyphenyl) cyclohexyl]-4-methoxycarbonylbenzamide are dissolved in 50 ml of acetonitrile and 1.0 ml of phosphorus oxychloride and stirred at 50° C. for 8 h. The reaction mixture is poured into 100 ml of saturated sodium bicarbonate solution and extracted with ethyl acetate. The organic phase is washed with sodium bicarbonate solution and water, dried with sodium sulfate and concentrated. The residue is recrystallized from ethyl acetate/petroleum ether. This gives 660 mg (38.6% of Th.) of the title compound of m.p.: 121.5–122.5° C.

EF: $C_{23}H_{25}NO_4$; MW: 379.46

Elemental analysis: Calc.: C 72.80 H 6.64 N 3.69 Found: C 72.70 H 6.61 N 3.58

Starting from the corresponding starting materials described below, the following compounds are obtained analogously by using the procedure of Example 1:

2. (+/−)-cis-8,9-diethoxy-6-[4-(methoxycarbonyl) phenyl]-1,2,3,4,4a,10b-hexahydrophenanthridine
   m.p.: 136–137° C., Yield 59.8% of Th.
   EF: $C_{25}H_{29}NO_4$; MW: 407.51
   Elemental analysis: Calc.: C 73.69 H 7.18 N 3.44 Found: C 73.83 H 7.27 N 3.59

3. (+/−)-cis-9-difluoromethoxy-8-methoxy-6-[4-(methoxycarbonyl)phenyl]-1,2,3,4,4a,10b-hexahydrophenanthridine
   m.p.: 126–127° C., Yield 34.5% of Th.
   EF: $C_{23}H_{23}F_2NO_4$; MW: 415.44
   Elemental analysis: Calc.: C 66.50 H 5.58 N 3.37 F 9.15 Found: C 66.59 H 5.55 N 3.36 F 9.21

4. (+/−)-cis-9-ethoxy-8-methoxy-6-[4-(methoxycarbonyl) phenyl]-1,2,3,4,4a,10b-hexahydrophenanthridine
   m.p.: 143.5–144.5° C., Yield: 88.6% of Th.
   EF: $C_{24}H_{27}NO_4$; MW: 393.48
   Elemental analysis: Calc.: C 73.26 H 6.92 N 3.56 Found: C 73.24 H 6.92 N 3.70

5. (+/−)-cis-8-ethoxy-9-methoxy-6-[4-(methoxycarbonyl) phenyl]-1,2,3,4,4a,10b-hexahydrophenanthridine
   m.p.: 123–124.5° C.; Yield: 81.9% of Th.
   EF: $C_{24}H_{27}NO_4$; MW: 393.48
   Elemental analysis: Calc.: C 73.26 H 6.92 N 3.56 Found: C 73.37 H 6.97 N 3.56

6. (+/−)-cis-8,9-diethoxy-6-[3-(methoxycarbonyl) phenyl]-1,2,3,4,4a,10b-hexahydrophenanthridine
   Oil; Yield: 40.4% of Th.
   EF: $C_{25}H_{29}NO_4$; MW: 407.51
   Elemental analysis: Calc.: C 73.69 H 7.17 N 3.44 Found: C 73.10 H 7.10 N 3.33

7. (+/−)-cis-8,9-diethoxy-6-[2-(methoxycarbonyl) phenyl]-1,2,3,4,4a,10b-hexahydrophenanthridine
   Oil; Yield: 19.2% of Th.
   EF: $C_{25}H_{29}NO_4$; MW: 407.51
   Elemental analysis×0.5 $H_2O$: Calc.: C 72.79 H 7.26 N 3.36 Found: C 71.90 H 7.26 N 3.20

8. (+/−)-trans-8,9-dimethoxy-6-[4-(methoxycarbonyl) phenyl]-1,2,3,4,4a,10b-hexahydrophenanthridine
   m.p.: 212–214° C.; Yield: 52.7% of Th.
   EF: $C_{23}H_{25}NO_4$; MW: 379.46
   Elemental analysis: Calc.: C 72.80 H 6.64 N 3.69 Found: C 72.69 H 6.68 N 3.67

9. (−)-cis-8,9-diethoxy-6-[4-(methoxycarbonyl)phenyl]-1,2,3,4,4a,10b-hexahydrophenanthridine
   m.p.: 92–95° C.; Yield: 46.6% of Th.
   EF: $C_{25}H_{29}NO_4$; MW: 407.51
   Optical rotation: $[\alpha]_D^{20}$ −61.26° (c=0.475, ethanol)
   Elemental analysis: Calc.: C 73.69 H 7.17 N 3.44 Found: C 73.55 H 7.25 N 3.35

10. (+)-cis-8,9-diethoxy-6-[4-(methoxycarbonyl)phenyl]-1,2,3,4,4a,10b-hexahydrophenanthridine
    m.p.: 92–125° C.; Yield: 48.2% of Th.
    EF: $C_{25}H_{29}NO_4$; MW: 407.51
    Optical rotation: $[\alpha]D_D^{20}$ +60.08° (c=0.23, ethanol)
    Elemental analysis: Calc.: C 73.69 H 7.17 N 3.44 Found: C 73.66 H 7.20 N 3.60

11. (−)-cis-8,9-dimethoxy-6-[4-(methoxycarbonyl) phenyl]-1,2,3,4,4a,10b-hexahydrophenanthridine
    Oil which solidifies; Yield: 58.1% of Th.
    EF: $C_{23}H_{25}NO_4$; MW: 379.46
    Optical rotation: $[\alpha]_D^{20}$ −90.0° (c=0.2, ethanol)
    Elemental analysis: Calc.: C 72.80 H 6.64 N 3.69 Found: C 72.80 H 6.90 N 3.54

12. (+)-cis-8,9-dimethoxy-6-[4-(methoxycarbonyl) phenyl]-1,2,3,4,4a,10b-hexahydrophenanthridine
    Oil which solidifies; Yield: 86.9% of Th.
    EF: $C_{23}H_{25}NO_4$; MW: 379.46
    Optical rotation: $[\alpha]_D^{20}$ +83.9° (c=0.2, ethanol)
    Elemental analysis: Calc.: C 72.80 H 6.64 N 3.69 Found: C 72.99 H 6.73 N 3.66

13. (+/−)-cis-8,9-dimethoxy-6-[4-(cyclopropylmethoxycarbonyl)phenyl]-1,2,3,4,4a,10b-hexahydrophenanthridine
    2.0 g of (+/−)-cis-8,9-dimethoxy-6-(4-carboxyphenyl)-1,2,3,4,4a,10b-hexahydrophenanthridine are suspended in 12.0 ml of cyclopropylmethanol, admixed with 1.0 ml of thionyl chloride and stirred at 50° C. for 4 days. The solution is concentrated under reduced pressure and the residue is partitioned between ethyl acetate and dilute sodium bicarbonate solution. The organic phase is dried with sodium sulfate and concentrated. The residue is recrystallized from ethyl acetate. This gives 1.33 g (63.7% of Th.) of the title compound of m.p.: 147–148° C.
    EF: $C_{26}H_{29}NO_4$; MW: 419.53
    Elemental analysis: Calc.: C 74.44 H 6.97 N 3.34 Found: C 74.13 H 6.84 N 3.48

14. (+/−)-cis-6-(4-carboxyphenyl)-8,9-diethoxy-1,2,3,4,4a,10b-hexahydrophenanthridine hydrochloride
    220 mg of (+/−)-cis-8,9-diethoxy-6-[4-(methoxycarbonyl)phenyl]-1,2,3,4,4a,10b-hexahydrophenanthridine are dissolved in 3.0 ml of conc. hydrochloric acid and 5.0 ml of water and stirred at 80° C. for 4 h. The precipitate which is formed on cooling is filtered off with suction and dried. This gives 135 mg (58.1% of Th.) of the title compound of m.p.: 269° C.
    EF: $C_{24}H_{27}NO_4 \times HCl$; MW: 429.95
    Elemental analysis: Calc.: C 67.05 H 6.56 Cl 8.25 N 3.26 Found: C 66.90 H 6.51 Cl 8.22 N 3.11

Starting from the corresponding starting materials described above, the following compounds are obtained analogously by using the procedure of Example 14:

15. (+/−)-cis-6-(4-carboxyphenyl)-8,9-dimethoxy-1,2,3,4,4a,10b-hexahydrophenanthridine hydrochloride
    m.p.: 220° C. (decomp.); Yield: 65% of Th.
    EF: $C_{22}H_{23}NO_4 \times HCl$; MW: 401.89
    Elemental analysis: Calc.: C 65.75 H 6.02 Cl 8.82 N 3.48 Found: C 65.63 H 6.06 Cl 8.58 N 3.60

16. (+/−)-cis-6-(4-carboxyphenyl)-9-ethoxy-8-methoxy-1,2,3,4,4a,10b-hexahydrophenanthridine hydrochloride
    m.p.: 180° C. (decomp.); Yield: 53.4% of Th.
    EF: $C_{23}H_{25}NO_4 \times HCl$; MW: 415.92
    Elemental analysis×2.5 $H_2O$: Calc.: C 59.93 H 6.78 N 3.03 Cl 7.68 Found: C 59.70 H 6.57 N 3.18 Cl 7.71

17. (+/−)-cis-6-(4-carboxyphenyl)-8-ethoxy-9-methoxy-1,2,3,4,4a,10b-hexahydrophenanthridine hydrochloride
    m.p.: >250° C., Yield: 32.4% of Th.
    EF: $C_{23}H_{25}NO_4 \times HCl$; MW: 415.92
    Elemental analysis: Calc.: C 66.42 H 6.30 N 3.37 Cl 8.52 Found: C 66.37 H 6.31 N 3.24 Cl 8.79

18. (+/−)-cis-6-(3-carboxyphenyl)-8,9-diethoxy-1,2,3,4,4a,10b-hexahydrophenanthridine hydrochloride m.p.: 259–260° C., Yield: 32.6% of Th.
    EF: $C_{24}H_{27}NO_4 \times HCl$; MW: 429.95
    Elemental analysis: Calc.: C 67.05 H 6.56 N 3.26 Cl 8.25 Found: C 67.05 H 6.67 N 3.19 Cl 8.22

19. (+/−)-cis-6-(4-carboxyphenyl)-9-difluoromethoxy-8-methoxy-1,2,3,4,4a,10b-hexahydrophenanthridine hydrochloride
    m.p.: 170° C. (decomp.), Yield: 69.8% of Th.
    EF: $C_{22}H_{21}F_2NO_4 \times HCl$; MW: 437.88
    Elemental analysis×$C_2H_5OH$: Calc.: C 59.57 H 5.83 N 2.89 F 7.85 Cl 7.33 Found: C 59.39 H 5.76 N 2.65 F 8.00 Cl 7.10

20. (+/−)-cis-6-[4-(N-methylaminocarbonyl)phenyl]-8,9-dimethoxy-1,2,3,4,4a,10b-hexahydrophenanthridine 680 mg of (+/−)-cis-8,9-dimethoxy-6-[4-(methoxycarbonyl)phenyl]-1,2,3,4,4a,10b-hexahydrophenanthridine with 25 mg of sodium cyanide in 13 ml of 9 molar methylamine solution in ethanol are heated to 90° C. in an autoclave for 10 h. The solution is concentrated under reduced pressure and the residue is taken up in methylene chloride and extracted with water. The organic phase is dried with sodium sulfate, the solvent is removed under reduced pressure and the residue is treated with diethyl ether, filtered off with suction and dried. This gives 380 mg (56.1 % of Th.) of the title compound of m.p. 209–211° C.

EF: $C_{23}H_{26}N_2O_3$; MW: 378.48

Elemental analysis: Calc.: C 72.99 H 6.92 N 7.40 Found: C 72.64 H 6.99 N 7.44

Starting materials

A1. (+/−)-cis-N-[2-(3,4-dimethoxyphenyl)cyclohexyl]-4-methoxycarbonylbenzamide 2.6 g of (+/−)-cis-1,2-dimethoxy-4-(2-aminocyclohexyl)benzene are dissolved in 20 ml of methylene chloride and 1 ml of triethylamine. At RT, a solution of 2.4 g of 4-methoxycarbonylbenzoyl chloride in 30 ml of methylene chloride is added dropwise over a period of 3 h, and the mixture is stirred for 1 h and then extracted with 50 ml each of water, 2 N hydrochloric acid, sat. sodium bicarbonate solution and once more with water. The organic phase is dried with sodium sulfate, concentrated and crystallized from ethyl acetate. This gives 2.0 g (45.5% of Th.) of the title compound of m.p. 139–143° C.

Starting from the corresponding starting materials described below, the following compounds are obtained analogously by using the procedure of Example A1:

A2. (+/−)-cis-N-[2-(3-difluoromethoxy-4-methoxyphenyl)cyclohexyl]-4-methoxycarbonylbenzamide Oil; Yield 96.5% of Th.

A3. (+/−)-cis-N-[2-(3,4-diethoxyphenyl)cyclohexyl]-4-methoxycarbonylbenzamide

Oil; Yield 58.7% of Th.

A4. (+/−)-cis-N-[2-(3-ethoxy-4-methoxyphenyl)cyclohexyl]-4-methoxycarbonylbenzamide m.p.: 151.5–152.5° C.; Yield: 78.9% of Th.

A5. (+/−)-cis-N-[2-(2-ethoxy-3-methoxyphenyl)cyclohexyl]-4-methoxycarbonylbenzamide m.p.: 126.5–127.5° C.; Yield: 58.7% of Th.

A6. (+/−)-cis-N-[2-(2,3-diethoxyphenyl)cyclohexyl]-3-methoxycarbonylbenzamide

Oil; Yield: 96.27% of Th.

A7. (+/−)-cis-N-[2-(2,3-diethoxyphenyl)cyclohexyl]-2-methoxycarbonylbenzamide m.p.: 144–144.5° C.; Yield: 59.6% of Th.

A8. (+/−)-trans-N-[2-(3,4-dimethoxyphenyl)cyclohexyl]-4-methoxycarbonylbenzamide m.p.: 189–193° C.; Yield: 48.0% of Th.

A9. (−)-cis-N-[2-(3,4-diethoxyphenyl)cyclohexyl]-4-methoxycarbonylbenzamide m.p.: 122–124° C.; Yield: 80.15% of Th.

Optical rotation: $[\alpha]_D^{20}$ −137.3° (c=0.11, ethanol)

A10. (+)-cis-N-[2-(3,4-diethoxyphenyl)cyclohexyl]-4-methoxycarbonylbenzamide m.p.: 123–125° C.; Yield: 86.75% of Th.

Optical rotation: $[\alpha]_D^{20}$ +134.8° (c=0.135, ethanol)

A11. (−)-cis-N-[2-(3,4-dimethoxyphenyl)cyclohexyl]-4-methoxycarbonylbenzamide m.p.: 154.5–156° C.; Yield: 85.2% of Th.

Optical rotation: $[\alpha]_D^{20}$ −167.7° (c=0.2, ethanol)

A12. (+)-cis-N-[2-(3,4-dimethoxyphenyl)cyclohexyl]-4-methoxycarbonylbenzamide m.p.: 153.5–154.5° C.; Yield: 85.1% of Th.

Optical rotation: $[\alpha]_D^{20}$ +165° (c=0.2, ethanol)

B1. (+/−)-cis-1,2-dimethoxy-4-(2-aminocyclohexyl)benzene 8.5 g of (+/−)-cis-1,2-dimethoxy-4-(2-nitrocyclohexyl)benzene are dissolved in 400 ml of methanol and, at RT, admixed in portions with 7 ml of hydrazine hydrate and 2.5 g of Raney nickel over a period of 8 h. The reaction mixture is stirred at RT overnight and then filtered, the filtrate is concentrated and the residue is chromatographed over silica gel using a mixture of toluene/ethyl acetate/triethylamine= 4/2/0.5.

Oil; Yield 74.4% of Th.

Starting from the starting materials described below, the following compounds are obtained by using the procedure of Example B1:

B2. (+/−)-trans-1,2-dimethoxy-4-(2-aminocyclohexyl)benzene

Oil; Yield: 65.9% of Th.

B3. (+/−)-cis-1,2-diethoxy-4-(2-aminocyclohexyl)benzene

Oil; Yield: 42.8% of Th.

B4. (+/−)-cis-2-difluoromethoxy-1-methoxy-4-(2-aminocyclohexyl)benzene 14.6 g of (+/−)-cis-2-difluoromethoxy-1-methoxy-4-(2-nitrocyclohex-4-enyl)benzene are dissovled in 170 ml of ethanol, admixed with 3.0 g of Raney nickel and hydrogenated in an autoclave at a hydrogen pressure of 50 bar for 9 days. The suspension is filtered, the solvent is removed under reduced pressure and the residue is chromatographed over silica gel using a mixture of toluene/dioxane/triethylamine 3/1/0.5. Concentration of the appropriate fractions gives 3.4 g (25.7% of Th.) of the title compound as an oil.

Starting from the appropriate starting materials described below, the following compounds are obtained analogously by using the procedure of Example B4:

B5. (+/−)-cis-2-ethoxy-1-methoxy-4-(2-aminocyclohexyl)benzene

Oil; Yield quantitative B6. (+/−)-cis-1-ethoxy-2-methoxy-4-(2-aminocyclohexyl)benzene Oil; Yield quantitative B7. (−)-cis-1,2-diethoxy-4-(2-aminocyclohexyl)benzene hydrochloride 2.2 g of (−)-cis-1,2-diethoxy-4-[2-(1-phenylethyl)aminocyclohexyl]benzene are suspended in 50 ml of ethanol, admixed with 270 mg of 10% palladium on carbon and hydrogenated at 50° C. and a hydrogen pressure of 50 bar for 6 days. The catalyst is filtered off, the solution is concentrated under reduced pressure and the product that crystallizes is filtered off with suction and dried.

m.p.: 145–147° C.; Yield: 59.0% of Th.

Optical rotation: $[\alpha]_D^{20}$ −60° (c=0.12, ethanol)

Starting from the appropriate starting materials described below, the following compounds are obtained analogously by using the procedure of Example B7:

B8. (+)-cis-1,2-diethoxy-4-(2-aminocyclohexyl)benzene hydrochloride m.p.: 149–151° C.; Yield: 52.9% of Th.

Optical rotation: $[\alpha]_D^{20}$ +70° (c=0.21, ethanol)

B9. (−)-cis-1,2-dimethoxy-4-(2-aminocyclohexyl)benzene 12.0 g of (+/−)-cis-1,2-dimethoxy-4-(2-aminocyclohexyl)benzene and 6.2 g of (−)mandelic acid are dissolved in 420 ml of dioxane and 60 ml of tetrahydrofuran and stirred at RT overnight. The solid is filtered off with suction, dried, admixed with 100 ml of saturated sodium bicarbonate solution and extracted with ethyl acetate. The organic phase is dried with sodium sulfate and concentrated under reduced pressure. This gives 4.8 g (40.0% of Th.) of the title compound of m.p.: 80–81.5° C.

Optical rotation: $[\alpha]_D^{20}$ −58.5° (c=1, ethanol)

Starting from the appropriate starting materials described below, the following compounds are obtained analogously using the procedure of Example B9:

B10. (+)-cis-1,2-dimethoxy-4-(2-aminocyclohexyl) benzene m.p.: 68–69° C.; Yield: 37.2% of Th.

Optical rotation: $[\alpha]_D^{20}$ +59.2° (c=1, ethanol)

C1. (−)-cis-1,2-diethoxy-4-[2-(1-phenylethyl) aminocyclohexyl]benzene 4.0 g of 2-(3,4-diethoxyphenyl)cyclohexanone, 2.0 ml of R-(+)-1-phenethylamine and 20 mg of toluenesulfonic acid are dissolved in 150 ml of toluene and heated under reflux using a water separator for 18 h. The solution is concentrated under reduced pressure and the residue is taken up in 200 ml of ethanol, admixed with 5 g of Raney nickel (moistened with ethanol) and hydrogenated at RT and 30–60 bar of hydrogen pressure for 10 days. The catalyst is filtered off with suction, the solution is concentrated under reduced pressure and the residue is chromatographed over silica gel using a mixture of toluene/dioxane/triethylamine at a ratio of 20/2/1. Concentration of the appropriate eluate fractions gives 2.15 g (38.4% of Th.) of the title compound as an oil.

Optical rotation: $[\alpha]_D^{20}$ −3.7° (c=0.27, ethanol)

Starting from the appropriate starting materials described below, the following compounds are obtained analogously by using the procedure of Example C1:

C2. (+)-cis-1,2-diethoxy-4-[2-(1-phenylethyl) aminocyclohexyl]benzene

Starting from 2-(3,4-diethoxyphenyl)cyclohexanone and S-(−)-1-phenethylamine, the title compound is obtained as an oil.

Yield: 64.6% of Th.

Optical rotation: $[\alpha]_D^{20}$+7.1° (c=0.56, ethanol)

D1. 2-(3.4-diethoxyphenyl)cyclohexanone 10.2 g of 2-(3,4-diethoxyphenyl)cyclohex-4-enone in 600 ml of tetrahydrofuran are admixed with 1.5 ml of conc. hydrochloric acid and 400 mg of 10% palladium on carbon and hydrogenated. The catalyst is filtered off, the solution is concentrated under reduced pressure and the residue is chromatographed over silica gel using a mixture of petroleum ether/ethyl acetate in a ratio of 2/1. Concentration of the appropriate eluate fractions gives 8.25 g (80.9% of Th.) of the title compound as an oil which solidifies.

E1. 2-(3,4-diethoxyphenyl)cyclohex-4-enone 15.0 g of (+/−)-trans-1,2-diethoxy-4-(2-nitrocyclohex-4-enyl)benzene are dissolved in 375 ml of ethanol and added dropwise to 42 ml of 20% strength sodium ethoxide solution. The mixture is stirred at RT for 20 min. and then added dropwise to an ice-cooled solution of 67.5 ml of conc. hydrochloric acid and 1.35 g of urea in 225 ml of water and 170 ml of ethanol. The solution is extracted with water/dichloromethane and the organic phase is dried with sodium sulfate and concentrated under reduced pressure. The residue is chromatographed over silica gel using petroleum ether/ethyl acetate in a ratio of 2/1. Concentration of the appropriate eluate fractions gives 10.33 g (77.1% of Th.) of the title compound as an oil.

F1. (+/−)-cis-1,2-dimethoxy-4-(2-nitrocyclohexyl) benzene 8.4 g of (+/−)-cis-1,2-dimethoxy-4-(2-nitrocyclohex-4-enyl)benzene are dissolved in 450 ml of methanol, admixed with 2 ml of conc. hydrochloric acid and hydrogenated after the addition of 500 mg of Pd/C 10%. The reaction mixture is filtered and the filtrate is concentrated. M.p.: 84–86.5° C.; Yield quantitative.

Starting from the appropriate starting materials described below, the following compounds are obtained analogously by using the procedure of Example F1:

F2. (+/−)-cis-1,2-diethoxy-4-(2-nitrocyclohexyl)benzene

Oil; Yield: 96.5% of Th.

F3. (+/−)-trans-1,2-dimethoxy-4-(2-nitrocyclohexyl) benzene

Oil; Yield: 47.0% of Th.

G1. (+/−)-cis-1,2-dimethoxy-4-(2-nitrocyclohex-4-enyl) benzene 10.0 g of (+/−)-trans-1,2-dimethoxy-4-(2-nitrocyclohex-4-enyl)benzene and 20.0 g of potassium hydroxide are dissolved in 150 ml of ethanol and 35 ml of dimethylformamide. A solution of 17.5 ml of conc. sulfuric acid in 60 ml of ethanol is subsequently added dropwise in such a way that the internal temperature does not exceed 4° C. The mixture is stirred for 1 h and then poured onto 1 l of ice-water, the precipitate is filtered off with suction, washed with water and dried and the crude product is recrystallized from ethanol. m.p.: 82.5–84° C.; Yield 86% of Th.

Starting from the appropriate starting materials described below, the following compounds are obtained analogously by using the procedure of Example G1:

G2. (+/−)-cis-2-difluoromethoxy-1-methoxy-4-(2-nitrocyclohex-4-enyl)benzene

Oil; Yield quantitative

G3. (+/−)-cis-1,2-diethoxy-4-(2-nitrocyclohex-4-enyl) benzene

Oil; Yield 96.5% of Th.

G4. (+/−)-cis-2-ethoxy-1-methoxy-4-(2-nitrocyclohex-4-enyl)benzene m.p.: 66–67° C.; Yield: 97.2% of Th.

G5. (+/−)-cis-1-ethoxy-2-methoxy-4-(2-nitrocyclohex-4-enyl)benzene m.p.: 96–97° C.; Yield 95.8% of Th.

H1. (+/−)-trans-1,2-dimethoxy-4-(2-nitrocyclohex-4-enyl)benzene 50.0 g of 3,4-dimethoxy-ω-nitrostyrene and 1.0 g (9.1 mmol) of hydroquinone are suspended in 200 ml of abs. toluene and, at −70° C., admixed with 55.0 g (1.02 mol) of liquid 1,3-butadiene. The mixture is stirred in an autoclave at 160° C. for 6 days and then cooled. Some of the solvent is removed using a rotary evaporator, and the resulting precipitate is filtered off with suction and recrystallized from ethanol. M.p.: 113.5–115.5° C.; Yield 76.3% of Th.

Starting from the appropriate starting materials described below, the following compounds are obtained analogously by using the procedure of Example H1:

H2. (+/−)-trans-2-difluoromethoxy-1-methoxy-4-(2-nitrocyclohex-4-enyl)benzene m.p.: 100–102° C.; Yield 62.3% of Th.

H3. (+/−)-trans-1,2-diethoxy-4-(2-nitrocyclohex-4-enyl) benzene m.p.: 80–81.5° C.; Yield 59.8 % of Th.

H4. (+/−)-trans-2-ethoxy-1-methoxy-4-(2-nitrocyclohex-4-enyl)benzene m.p.: 129–130° C.; Yield: 75.7% of Th.

H5. (+/−)-trans-1-ethoxy-2-methoxy-4-(2-nitrocyclohex-4-enyl)benzene m.p.: 70.5–72° C.; Yield: 66.8% of Th.

I1. 3,4-dimethoxy-ω-nitrostyrene 207.0 g of 3,4-dimethoxybenzaldehyde, 100.0 g of ammonium acetate and 125 ml of nitromethane are heated to the boil in 1.0 l of glacial acetic acid for 3–4 h. The mixture is cooled in an ice bath and the precipitate is filtered off with suction, rinsed with glacial acetic acid and petroleum ether and dried.

M.p.: 140–141° C. Yield: 179.0 g (68.5% of Th.)

Starting from the starting materials described below or known from the literature, the following compounds are obtained analogously by using the procedure of Example I1:

I2. 3-difluoromethoxy-4-methoxy-ω-nitrostyrene
m.p.: 120–123° C.; Yield 24.8% of Th.

I3. 3,4-diethoxy-ω-nitrostyrene
m.p.: 136–136.5° C.; Yield: 76.2% of Th.

I4. 3-ethoxy-4-methoxy-ω-nitrostyrene
m.p.: 132–133° C.; Yield: 70.3% of Th.

I5. 4-ethoxy-3-methoxy-ω-nitrostyrene
m.p.: 147–148.5° C.; Yield: 68.6% of Th.

J. 3-difluoromethoxy-4-methoxybenzaldehyde

With vigorous stirring, chlorodifluoromethane is introduced into a mixture of 200 g of isovanillin, 6.7 g of benzyltrimethylammonium chloride, 314 g of 50% strength aqueous sodium hydroxide solution and 2 l of dioxane for approximately 2 h. The mixture is subsequently partitioned between ice-water and ethyl acetate, the organic phase is separated off, the aqueous phase is extracted twice with ethyl acetate and the combined organic phases are dried over magnesium sulfate and concentrated under reduced pressure. To remove unreacted isovanillin, the oil is chromatographed over neutral silica gel using toluene. Evaporation of the eluate gives 249 g of 3-difluoromethoxy-4-methoxybenzaldehyde as an oil.

Commercial Utility

The compounds according to the invention have valuable pharmacological properties which make them commercially utilizable. As selective cyclic nucleotide phosphodiesterase (PDE) inhibitors (namely of type IV), they are suitable on the one hand as bronchial therapeutics (for the treatment of airway obstructions on account of their dilating action but also on account of their respiratory rate- or respiratory drive-increasing action) and for the elimination of erectile dysfunction on account of the vasodilating action, but on the other hand especially for the treatment of disorders, in particular of an inflammatory nature, e.g. of the airways (asthma prophylaxis), of the skin, of the intestine, of the eyes, of the central nervous system and of the joints which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen free radicals and proteases. The compounds according to the invention here are distinguished by low toxicity, good enteral absorption (high bioavailability), great therapeutic breadth and the absence of significant side effects.

On account of their PDE-inhibiting properties, the compounds according to the invention can be employed as therapeutics in human and veterinary medicine, where they can be used, for example, for the treatment and prophylaxis of the following illnesses: acute and chronic (in particular inflammatory and allergen-induced) respiratory diseases of various origins (bronchitis, allergic bronchitis, bronchial asthma); dermatoses (especially of proliferative, inflammatory and allergic nature) such as, for example, psoriasis (vulgaris), toxic and allergic contact eczema, atopic eczema, seborrheic eczema, lichen simplex, sunburn, pruritus in the anogenital area, alopecia areata, hypertrophic scars, discoid lupus erythematosus, follicular and widespread pyodermias, endogenous and exogenous acne, acne rosacea and other proliferative, inflammatory and allergic skin disorders; disorders which are based on an excessive release of TNF and leukotrienes, i.e., for example, disorders of the arthritic type (rheumatoid arthritis, rheumatoid spondylitis, osteoarthritis and other arthritic conditions), disorders of the immune system (AIDS, multiple sclerosis), types of shock [septic shock, endotoxin shock, Gram-negative sepsis, toxic shock syndrome and ARDS (adult respiratory distress syndrome)] and also generalized inflammations in the gastrointestinal region (Crohn's disease and ulcerative colitis); disorders which are based on allergic and/or chronic, faulty immunological reactions in the region of the upper airways (pharynx, nose) and the adjacent regions (paranasal sinuses, eyes), such as, for example, allergic rhinitis/sinusitis, chronic rhinitis/sinusitis, allergic conjunctivitis and also nasal polyps; but also diseases of the heart which can be treated by PDE inhibitors, such as, for example, cardiac insufficiency, or disorders which can be treated on account of the tissue-relaxant action of the PDE inhibitors, such as, for example, erectile dysfunction or colics of the kidneys and the ureters in connection with kidney stones.

The invention further relates to a method for the treatment of mammals, including humans, who are suffering from one of the abovementioned illnesses. The process comprises administering to the sick mammal a therapeutically efficacious and pharmacologically tolerable amount of one or more of the compounds according to the invention.

The invention furthermore relates to the compounds according to the invention for use in the treatment and/or prophylaxis of the illnesses mentioned.

The invention likewise relates to the use of the compounds according to the invention for the production of medicaments which are employed for the treatment and/or prophylaxis of the illnesses mentioned.

Furthermore, the invention relates to medicaments which contain one or more of the compounds according to the invention for the treatment and/or prophylaxis of the illnesses mentioned.

The medicaments are prepared by methods known per se which are familiar to the person skilled in the art. As medicaments, the compounds according to the invention (=active compounds) are either employed as such, or preferably in combination with suitable pharmaceutical auxiliaries, e.g. in the form of tablets, coated tablets, capsules, suppositories, patches, emulsions, suspensions, gels or solutions, the active compound content advantageously being between 0.1 and 95%.

The person skilled in the art is familiar on the basis of his expert knowledge with the auxiliaries which are suitable for the desired pharmaceutical formulations. Beside solvents, gel-forming agents, ointment bases and other active compound carriers, it is possible to use, for example, antioxidants, dispersants, emulsifiers, preservatives, solubilizers or permeation promoters.

For the treatment of disorders of the respiratory tract, the compounds according to the invention are preferably also administered by inhalation. For this purpose, these are either administered directly as a powder (preferably in micronized form) or by atomizing solutions or suspensions which contain them. With respect to the preparations and administration forms, reference is made, for example, to the details in European Patent 163 965.

For the treatment of dermatoses, the compounds according to the invention are applied, in particular, in the form of those medicaments which are suitable for topical application. For the production of the medicaments, the compounds according to the invention (=active compounds) are preferably mixed with suitable pharmaceutical auxiliaries and additionally processed to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are prepared by methods known per se. The dosage of the active compounds takes place in the order of magnitude customary for PDE inhibitors. Thus topical application forms (such as, for example, ointments) for the treatment of dermatoses contain the active compounds in a concentration of, for example, 0.1–99%. The dose for administration by inhalation is customarily between 0.01 and 1 mg per spray burst. The customary dose in the case of systemic therapy (p.o. or i.v.) is between 0.1 and 200 mg per administration.

Biological Investigations

In the investigation of PDE IV inhibition at the cellular level, the activation of inflammatory cells has particular importance. As an example, the FMLP (N-formylmethionylleucylphenylalanine)-induced superoxide production of neutrophilic granulocytes may be mentioned, which can be measured as luminol-potentiated chemoluminescence [McPhail L C, Strum S L, Leone P A and Sozzani S, The neutrophil respiratory burst mechanism. In "Immunology Series" 1992, 57, 47–76; ed. Coffey R G (Marcel Decker, Inc., New York-Basel-Hong Kong)].

Substances which inhibit chemoluminescence and also cytokine secretion and the secretion of proinflammatory mediators from inflammatory cells, in particular neutrophilic and eosinophilic granulocytes, T lymphocytes, monocytes and macrophages, are those which inhibit PDE IV. This isoenzyme of the phosphodiesterase families is particularly represented in granulocytes. Its inhibition leads to an increase in the intracellular cyclic AMP concentration and thus to the inhibition of cellular activation. PDE IV inhibition by the substances according to the invention is thus a central indicator of the suppression of inflammatory processes. (Giembycz M A, Could isoenzyme-selective phosphodiesterase inhibitors render bronchodilatory therapy redundant in the treatment of bronchial asthma? Biochem Pharmacol 1992, 43, 2041–2051; Torphy T J et al., Phosphodiesterase inhibitors: new opportunities for treatment of asthma. Thorax 1991, 46, 512–523; Schudt C et al., Zardaverine: a cyclic AMP PDE III/IV inhibitor. In "New Drugs for Asthma Therapy", 379–402, Birkhäuser Verlag Basel 1991; Schudt C et al., Influence of selective phosphodiesterase inhibitors on human neutrophil functions and levels of cAMP and $Ca_i$, Naunyn-Schmiedebergs Arch Pharmacol 1991, 344, 682–690; Nielson C P et al., Effects of selective phosphodiesterase inhibitors on polymorphonuclear leukocyte respiratory burst. J. Allergy Clin Immunol 1990, 86, 801–808; Schade et al., The specific type III and IV phosphodiesterase inhibitor zardaverine suppress formation of tumor necrosis factor by macrophages. European Journal of Pharmacology 1993, 230, 9–14).

Inhibition of PDE IV Activity

Methodology

The activity test was carried out according to the method of Bauer and Schwabe, which was adapted to microtiter plates (Naunyn-Schmiedeberg's Arch. Pharmacol. 1980, 311, 193–198). The PDE reaction takes place here in the first step. In a second step, the resulting 5'-nucleotide is cleaved to give the uncharged nucleoside by a 5'-nucleotidase of the snake venom from Crotalus atrox. In the third step, the nucleoside is separated from the remaining charged substrate on ion exchange columns. Using 2 ml of 30 mM ammonium formate (pH 6.0), the columns are eluted directly into minivials to which is additionally added 2 ml of scintillator fluid for counting.

The inhibitory values determined for the compounds according to the invention follow from Table A below, in which the numbers of the compounds correspond to the numbers of the examples.

TABLE A

Inhibition of PDE IV Activity

| Compound | -log $IC_{50}$ |
|---|---|
| 1 | 7.39 |
| 2 | 8.84 |
| 3 | 7.73 |
| 4 | 8.73 |
| 5 | 7.02 |
| 6 | 8.14 |
| 7 | 6.34 |
| 8 | 5.92 |
| 9 | 8.52 |
| 10 | 7.48 |
| 11 | 7.52 |
| 12 | 4.95 |
| 13 | 7.39 |
| 14 | 8.27 |
| 15 | 6.81 |
| 16 | 8.66 |
| 17 | 6.79 |
| 18 | 7.69 |
| 19 | 7.55 |
| 20 | 5.18 |

What is claimed is:

1. A compound of the formula I

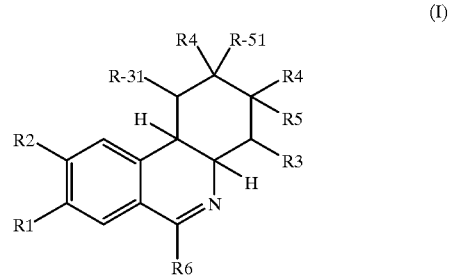

(I)

in which

R1 is hydroxy, 1–4C-alkoxy, 3–7C-cycloalkoxy or 3–7C-cycloalkylmethoxy or 1–4C-alkoxy which is completely or partially substituted by fluorine, R2 is hydroxy, 1–4C-alkoxy, 3–7C-cycloalkoxy or 3–7C-cycloalkylmethoxy or 1–4C-alkoxy which is completely or partially substituted by fluorine, or in which R1 and R2 together are a 1–2C-alkylenedioxy group, R3 is hydrogen or 1–4C-alkyl, R31 is hydrogen or 1–4C-alkyl, or in which R3 and R31 together are a 1–4C-alkylene group, R4 is hydrogen or 1–4C-alkyl, R5 is hydrogen R51 is hydrogen, or in which R5 and R51 together are an additional bond, R6 is a phenyl radical which is substituted by R7, where
R7 is COOR71 or CON(R72)R73 and R71 is hydrogen, 1–7C-alkyl, 3–7C-cycloalkyl or 3–7C-cycloalkylmethyl and R72 and R73 independently of one another are each hydrogen, 1–7C-alkyl, 3–7C-cycloalkyl or 3–7C-cycloalkylmethyl,
or a salt of this compound.

2. A compound of the formula I as claimed in claim 1, in which
R1 is 1–4C-alkoxy, 3–7C-cycloalkoxy or 3–7C-cycloalkylmethoxy or 1–2C-alkoxy which is completely or partially substituted by fluorine,
R2 is 1–4C-alkoxy, 3–7C-cycloalkoxy or 3–7C-cycloalkylmethoxy or 1–2C-alkoxy which is completely or partially substituted by fluorine,
R3 is hydrogen,
R31 is hydrogen,
or in which
R3 and R31 together are a 1–2C-alkylene group,
R4 is hydrogen or 1–4C-alkyl,
R5 is hydrogen,
R51 is hydrogen,
or in which
R5 and R51 together are an additional bond,
R6 is a phenyl radical which is substituted by R7, where
R7 is COOR71 or CON(R72)R73 and R71 is hydrogen, 1–7C-alkyl or 3–7C-cycloalkylmethyl and R72 and R73 independently of one another are each hydrogen or 1–7C-alkyl,
or a salt of this compound.

3. A compound of the formula I as claimed in claim 1, in which
R1 is 1–4C-alkoxy, 3–7C-cycloalkoxy or 1–2C-alkoxy which is completely or partially substituted by fluorine,
R2 is 1–4C-alkoxy, 3–7C-cycloalkoxy or 1–2C-alkoxy which is completely or partially substituted by fluorine,
R3 is hydrogen,
R31 is hydrogen,
or in which
R3 and R31 together are a 1–2C-alkylene group,
R4 is hydrogen or 1–4C-alkyl,
R5 is hydrogen,
R51 is hydrogen,
or in which
R5 and R51 together are an additional bond,
R6 is a phenyl radical which is substituted by R7, where
R7 is COOR71 or CON(R72)R73 and R71 is hydrogen, 1–7C-alkyl or 3–7C-cycloalkylmethyl and R72 and R73 independently of one another are each hydrogen or 1–4C-alkyl,
or a salt of this compound.

4. A compound of the formula I as claimed in claim 1, in which
R1 is methoxy, ethoxy or difluoromethoxy,
R2 is methoxy, ethoxy or difluoromethoxy,
R3 and R31 are each hydrogen,
R4 is hydrogen,
R5 and R51 are each hydrogen,
R6 is a phenyl radical which is substituted by R7, where
R7 is COOR71 or CON(R72)R73 and R71 is hydrogen or 1–4C-alkyl, R72 is hydrogen and R73 is 1–4C-alkyl,
and the salts of this compound.

5. A pharmaceutical composition comprising an effective amount of a compound as claimed in claim 1 or a pharmaceutically-acceptable salt thereof and a suitable pharmaceutical auxiliary or excipient.

6. In a method for compounding a pharmaceutical composition which comprises combining an active ingredient for treating a respiratory disease with a suitable pharmaceutical auxiliary or excipient, the improvement wherein the active ingredient is a compound as claimed in claim 1 or a pharmaceutically-acceptable salt thereof.

7. A method of treating an amenable respiratory disease which comprises administering an effective amount of a compound as claimed in claim 1, or a pharmaceutically-acceptable salt thereof, to a subject afflicted with such respiratory disease.

8. A compound of formula I as claimed in claim 1, in which
R1 is 1–4C-alkoxy,
R2 is 1–4C-alkoxy,
R3 is hydrogen,
R31 is hydrogen,
R4 is hydrogen,
R5 is hydrogen,
R51 is hydrogen,
R6 is a phenyl radical which is substituted by R7, where
R7 is COOR71 and
R71 is hydrogen,
or a salt thereof.

9. A pharmaceutical composition comprising an effective amount of a compound as claimed in claim 10 or a pharmaceutically-acceptable salt thereof, and a suitable pharmaceutical auxiliary or excipient.

10. In a method for compounding a pharmaceutical composition which comprises combining an active ingredient for treating a respiratory disease with a suitable pharmaceutical auxiliary or excipient, the improvement wherein the active ingredient is a compound as claimed in claim 10, or a pharmaceutically-acceptable salt thereof.

11. A method of treating an amenable respiratory disease which comprises administering an effective amount of a compound as claimed in claim 10 or a pharmaceutically-acceptable salt thereof to a subject afflicted with such respiratory disease.

12. The compound of formula I as claimed in claim 10 wherein R1 is methoxy and R2 is ethoxy, or a salt thereof.

* * * * *

UNITED STATES PATENT AND TRADEMARK OFFICE
CERTIFICATE OF CORRECTION

PATENT NO. : 6,191,138 B1
DATED : February 20, 2001
INVENTOR(S) : Beate Gutterer Page 1 of 1

It is certified that error appears in the above-identified patent and that said Letters Patent is hereby corrected as shown below:

Column 16,
Line 37 to 49, formula (I)

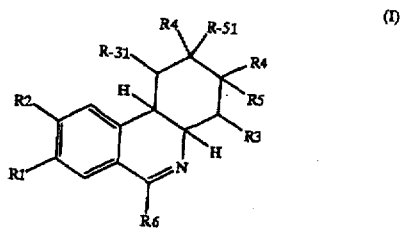

should read --

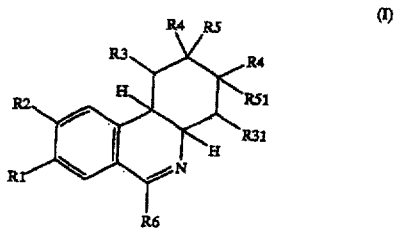

--.

Column 18,
Line 7, "and the salts" should read -- or a salt --; lines 37, 44, 48 and 51, "claim 10" (in each) should read -- claim 8 --.

Signed and Sealed this

Fourth Day of December, 2001

Attest:

NICHOLAS P. GODICI
Attesting Officer   Acting Director of the United States Patent and Trademark Office